(12) United States Patent
Fukai et al.

(10) Patent No.: US 9,327,013 B2
(45) Date of Patent: May 3, 2016

(54) ACTIVITY ENHANCER FOR ANTICANCER AGENT

(75) Inventors: Fumio Fukai, Tokyo (JP); Hiroaki Kodama, Saga (JP); Takuya Matsunaga, Kagawa (JP)

(73) Assignees: TOKYO UNIVERSITY OF SCIENCE FOUNDATION, Tokyo (JP); SAGA UNIVERSITY, Saga (JP); NATIONAL UNIVERSITY CORPORATION KAGAWA UNIVERSITY, Kagawa (JP)

( * ) Notice: Subject to any disclaimer, the term of this patent is extended or adjusted under 35 U.S.C. 154(b) by 116 days.

(21) Appl. No.: 14/004,196

(22) PCT Filed: Mar. 9, 2012

(86) PCT No.: PCT/JP2012/056186
§ 371 (c)(1),
(2), (4) Date: Sep. 10, 2013

(87) PCT Pub. No.: WO2012/124641
PCT Pub. Date: Sep. 20, 2012

(65) Prior Publication Data
US 2014/0005120 A1    Jan. 2, 2014

(30) Foreign Application Priority Data
Mar. 11, 2011 (JP) ................... 2011-054475

(51) Int. Cl.
*A61K 38/00* (2006.01)
*A61K 38/17* (2006.01)
*A61K 31/7068* (2006.01)
*C07K 14/78* (2006.01)
*C07K 14/47* (2006.01)

(52) U.S. Cl.
CPC ......... *A61K 38/1709* (2013.01); *A61K 31/7068* (2013.01); *C07K 14/47* (2013.01); *C07K 14/78* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,761,406 A * | 8/1988 | Flora et al. ................. | 514/86 |
| 2003/0040600 A1 * | 2/2003 | Kalafatis et al. ............ | 530/300 |
| 2009/0048178 A1 | 2/2009 | Matsumoto et al. | |

FOREIGN PATENT DOCUMENTS

| | | |
|---|---|---|
| JP | 06073093 | 3/1994 |
| JP | H10147600 A | 6/1998 |
| JP | 2000026490 A | 1/2000 |
| JP | 2006327980 A | 12/2006 |
| JP | 2009118854 A | 6/2009 |
| JP | 2010043087 A | 2/2010 |
| WO | WO-0108698 A1 | 2/2001 |
| WO | WO-2010140567 A1 | 12/2010 |

OTHER PUBLICATIONS

Dawson et al. Three Distinct D-Amino Acid Substitutions Confer Potent Antiangiogenic Activity on an Inactive Peptide Derived from a Thrombospondin-1 Type 1 Repeat. Molecular Pharmacology, 55:332-338 (1999).*

Galati et al., "Increased Resistance of Peptides to Serum Proteases by Modification of Their Amino Groups", Zeitschrift für Naturforschung. C, Journal of Biosciences, Jul. 1, 2003, pp. 558-561.

Search Report in European Application No. 12758028.0 dated Dec. 9, 2014.

International Search Report for PCT/JP2012/056186, dated May 22, 2012.

Hideki Mizunuma, "Why the Efficacy of Various Gnrh Agonish Formulations Varies?", Horm Front Gynecol, 1999, 6 (4), 108-9, p. 108, the 3rd paragraph.

Sayaka W., et al., Abrogation of Cell Adhesion-Mediated Drug Resistance (CAM-DR) of Acute Myelogenous Leukemia by Anti-Adhesive Peptide, FNII14, Peptide Science, 2010, vol. 2009, 325-8 See Fig.1.

Fukai, F. et al, Identification of the anti-adhesive site buried within the heparin-binding domain of fibronectin, J Biochem, 1997, vol. 121 No. 2, p. 189-92.

T. Matsunaga et al., Combination therapy of an anticancer drug with drug with the FNIII14 peptide of fibronectin effectively overcomes cell adhesion-mediated drug resistance of acute myelongenous leukemia, Leukemia, 2008, 22, 353-360.

Sung Yu Hong et al., Effect of D-Amino Acid Substitution on the Stability, the Secondary Structure, and the Activity of Membrane-Active Peptide, Biochem Pharmac0l., Dec. 1, 1999; 58(11), pp. 1775-1780.

S.J. Paterson, et al., Effectso F D-Aminoa CID Substitutioni N Dynorphina (I-9) on Bindinga T the u-, 6- and K-Sites, Neuropeptides., Dec. 1984, 5(1-3), pp. 177-180.

* cited by examiner

*Primary Examiner* — Maher Haddad
(74) *Attorney, Agent, or Firm* — Marshall, Gerstein & Borun LLP

(57) ABSTRACT

An activity enhancer for an anticancer agent includes, as an active ingredient, a D-form amino acid residue-containing FNIII14 polypeptide, the D-form amino acid residue-containing FNIII14 being a polypeptide FNIII14 represented by SEQ ID NO: 1 in which at least one of amino acid residues at positions 1 to 13 is a D-form amino acid residue. An anticancer composition includes the activity enhancer for an anticancer agent and an anticancer agent.

9 Claims, 4 Drawing Sheets

SEQUENCE LISTING

```
<160> NUMBER OF SEQ ID NOS: 5

<210> SEQ ID NO 1
<211> LENGTH: 21
<212> TYPE: PRT
<213> ORGANISM: Homo sapiens

<400> SEQUENCE: 1

Thr Glu Ala Thr Ile Thr Gly Leu Glu Pro Gly Thr Glu Tyr Thr Ile
1               5                   10                  15

Tyr Val Ile Ala Leu
            20

<210> SEQ ID NO 2
<211> LENGTH: 5
<212> TYPE: PRT
<213> ORGANISM: Homo sapiens

<400> SEQUENCE: 2

Tyr Gly Gly Phe Leu
1               5

<210> SEQ ID NO 3
<211> LENGTH: 8
<212> TYPE: PRT
<213> ORGANISM: Homo sapiens

<400> SEQUENCE: 3

Tyr Thr Ile Tyr Val Ile Ala Leu
1               5

<210> SEQ ID NO 4
<211> LENGTH: 5
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: D-Ala

<400> SEQUENCE: 4

Tyr Ala Gly Phe Leu
1               5

<210> SEQ ID NO 5
<211> LENGTH: 21
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: D-Glu

<400> SEQUENCE: 5

Thr Glu Ala Thr Ile Thr Gly Leu Glu Pro Gly Thr Glu Tyr Thr Ile
1               5                   10                  15

Tyr Val Ile Ala Leu
            20
```

ACTIVITY ENHANCER FOR ANTICANCER AGENT

TECHNICAL FIELD

The present invention relates to an activity enhancer for an anticancer agent.

BACKGROUND ART

Chemotherapy still plays an important role in cancer treatment today even though medical oncology has developed. In particular, chemotherapy is mainly employed in treatment of leukemia, and provides a higher therapeutic effect against leukemia than that against solid cancer. Especially, acute myeloid leukemia (AML) cells are known to be highly sensitive to drugs. For this reason, when remission-induction therapy is applied as treatment of AML, complete remission is observed in about 80% of cases. However, recurrence is observed in many cases, and a long-term survival rate achieved today is only from 30% to 40%. It is thought that recurrence is caused by a small number of leukemia cells remaining in the bone marrow of patients in a complete remission period after chemotherapy.

Leukemia cells in the non-adhered state in peripheral blood or body fluid are killed by anticancer agents with relatively high efficiency. However, it is known that leukemia cells in bone marrow adhere to extracellular matrixes (such as fibronectin (FN) or marrow stromal cells) via adhesion molecules (such as integrin), and thereby acquire resistance to anticancer agents, as a result of which a small number of leukemia cells remain even after chemotherapy. This phenomenon is called cell adhesion mediated drug resistance (CAM-DR), which is one of the most important problems to be solved in treatment of leukemia using anticancer agents.

Fibronectin is involved in adhesion and attachment-detachment of cells. Fibronectin is one of representative extracellular matrix protein molecules. Fibronectin is distributed in almost all tissues, and serves as a framework for building a tissue, as well as binds to adhesion molecules on the cell membrane and acts as a signal molecule for regulating cell functions.

A polypeptide constituting a fibronectin molecule is composed of type I, type II, and type III repetitive sequences. Among them, a fibronectin (FN) type III repeat (FNIII) is known to have various functions.

For example, FNIII is known to have a cell adhesion inhibitory activity (for example, see Japanese Patent Application Laid-Open (JP-A) No. H10-147600 and JP-A No. 2000-26490). JP-A No. H10-147600 mentions the possibility of an effect in terms of suppressing metastasis of cancer, but does not describe any working examples thereof. International Publication No. (WO) 01/08698 discloses an effect in terms of enhancing an anticancer activity based on the apoptosis induction activity of FNIII. However, the working examples disclosed in WO 01/08698 describe only the results of in vitro experiments, and does not study in vivo efficacy; therefore, there is no information about stability in blood and the like.

Furthermore, WO 01/08698 discloses only in vitro experiment, and includes no disclosure about effects in living organisms. Accordingly, practical judgment cannot be made with respect to an increase and enhancement of anticancer activity based on the apoptosis induction activity of FNIII.

Specifically, in FIGS. 1 to 8 of WO 01/08698, the effect achieved by mixing vincristine or actinomycin D with a polypeptide represented by SEQ ID NO: 2 is investigated using some cancer cells. However, data indicating practical hopefulness are not demonstrated; for example, the effect achieved by the addition is about 30% at most in FIGS. 1, 2, 3, 4, and 8, and an opposite effect is obtained depending on the concentration as in FIG. 2. Although FIGS. 5 and 7 illustrate an effect achieved by addition of the agent, the effect achieved by the agent itself does not show concentration dependence, and, therefore, the efficacy thereof cannot be evaluated. Only FIG. 6 suggests a tendency that the addition of polypeptide represented by SEQ ID NO: 2 exerts an effect on vincristine in a case in which GT3TKB cells derived from stomach cancer are used.

As is understood from the above, in consideration of clinical use in practice, it is thought that the addition of the polypeptide represented by SEQ ID NO: 2 exerts an effect only on a specific kind of cancer and a specific agent, and that the polypeptide represented by SEQ ID NO: 2 does not enhance the effects of all anticancer agents. Moreover, an effect achieved by using the polypeptide represented by SEQ ID NO: 2 with cytarabine or the like, which is a pyrimidine antimetabolite having another mechanism of action among anticancer agents, is not demonstrated.

JP-A No. 2006-327980 describes working examples which aim to cause remission in mice by using an antileukemic agent and a FNIII-like peptide in combination in animal experiments. However, the concentration of the FNIII-like peptide in the working examples is 1 mg, and no effect is confirmed at concentrations lower than this concentration.

In addition, experiments similar to those of JP-A No. 2006-327980 are reported in Leukemia (2008), Vol. 22, 353-360. However, this report demonstrates that even a modified FNIII-like peptide exhibits no improvement in physiological activity.

There are some reports about such a chemical modification. JP-A No. 2010-043087 reports that even when native HBHA was produced by genetic recombination in *E. coli*, the physiological activity thereof was different from that of HBHA produced by *Mycobacterium*, but inherent physiological activity thereof could be reproduced by methylation of a lysine group at the C-terminal. This merely indicates that the methylation led to recovery of the inherent activity, and does not demonstrate a higher effect than the inherent physiological activity. JP-A No. H6-73093 reports examples in which D-form amino acids such as Trp, His, or Phe were introduced for the purpose of eliminating defects of opioid analgesics such as dependence and tolerance. However, as described in JP-A No. H6-73093, these examples are not examples that achieved improvement in stability and activity as a compound. In addition, although one may think that the use of D-form amino acids prevents decomposition due to general inability of proteases to recognize D-form amino acids, it is also thought that the physiological activity of the peptide cannot be maintained due to a changed conformation of the obtained peptide. *Biochem Pharmcol.* 1999 Dec. 1; 58(11); 1775-80 reports that replacement of two residues at each of N-terminal and C-terminal with D-form amino acids resulted in increased stability in serum enzyme treatment, but did not increase the physiological activity. In *Neuropeptides*, 1984 December; 5(1-3): 177-80, it is reported that, for example, modification of enkephalin (Tyr-Gly-Gly-Phe-Leu (SEQ ID NO: 2)) from among the opioid peptide group to Tyr-D-Ala-Gly-Phe-Leu (SEQ ID NO: 4) by replacement of the second amino acid did not increase the activity.

SUMMARY OF INVENTION

Problem to be Solved by Invention

As discussed above, those that have achieved a requested level of stabilization and activity improvement of peptides are not known at present, and methods for improving the stability and activity of peptides to a requested level are not known, either.

As discussed above, there have been a desire for treatment that remedies the defects of fibronectin and related peptides thereof, and that eradicates acute myeloid leukemia or the like by combined administration with an anticancer agent or other anticancer agents.

Therefore, it is an object of the present invention to provide an activity enhancer capable of enhancing the activity of an anticancer agent that is used together with the activity enhancer, and a pharmaceutical composition containing the activity enhancer, with a view to eradicating malignant tumors having high probability of recurrence after chemotherapy, such as acute myeloid leukemia.

The present inventors conducted earnest research using a peptide that is essential for the physiological activity and that was selected to solve the problems described above, aiming to further improve the physiological activity, and to decrease the dose based on exertion of synergistic effects with many anticancer agents, and to achieve the stability of the peptide in blood. As a result, the inventors succeeded in finding a novel peptide that can solve the problems, and that is a derivative of peptide FNIII14, and, further, the inventors succeeded in eradication treatment of acute myeloid leukemia and remission treatment of other cancers using the peptide alone or in combination with an anticancer agent.

The present invention provides the following aspects.

[1] An activity enhancer for an anticancer agent, including, as an active ingredient, a D-form amino acid residue-containing FNIII14 polypeptide, the D-form amino acid residue-containing FNIII14 being a polypeptide FNIII14 represented by SEQ ID NO: 1 in which at least one of amino acid residues at positions 1 to 13 is a D-form amino acid residue.

[2] The activity enhancer for an anticancer agent according to [1], wherein the D-form amino acid residue-containing FNIII14 polypeptide includes from 1 to 6 D-form amino acid residues.

[3] The activity enhancer for an anticancer agent according to [1] or [2], wherein the D-form amino acid residue-containing FNIII14 polypeptide has the at least one D-form amino acid residue at at least one of positions 1 to 10 of the polypeptide represented by SEQ ID NO: 1.

[4] The activity enhancer for an anticancer agent according to any one of [1] to [3], wherein the D-form amino acid residue-containing FNIII14 polypeptide includes one D-form glutamic acid residue, and the one D-form glutamic acid residue corresponds to an amino acid residue at position 2 of the polypeptide represented by SEQ ID NO: 5.

[5] The activity enhancer for an anticancer agent according to any one of [1] to [4], wherein the D-form amino acid residue-containing FNIII14 polypeptide is a D-form amino acid residue-containing FNIII14 polypeptide multimer.

[6] The activity enhancer for an anticancer agent according to any one of [1] to [5], which is used in combination with an anticancer agent against leukemia.

[7] The activity enhancer for an anticancer agent according to any one of [1] to [6], wherein the anticancer agent is at least one selected from the group consisting of cytarabine (AraC), enocitabine, and elacytarabine.

[8] A pharmaceutical composition for treatment of a cancer, including the activity enhancer for an anticancer agent according to any one of [1] to [7] and a pharmaceutically acceptable carrier.

[9] The pharmaceutical composition according to [8], further including an anticancer agent.

[10] An anticancer therapeutic agent set including a first container section in which the activity enhancer for an anticancer agent according to any one of [1] to [7] is contained, and a second container section in which an anticancer agent is contained.

[11] A polypeptide that is either one of the following peptides:
(1) a polypeptide which is represented by SEQ ID NO: 1, and in which at least one of amino acid residues at positions 1 to 13 is a D-form amino acid residue; or
(2) a polypeptide which is a multimer, of which a constituent unit is the polypeptide (1).

[12] A method for treating a cancer, the method including administering, to a patient in need of treatment of a cancer, the activity enhancer for an anticancer agent according to any one of [1] to [5] or the pharmaceutical composition according to [8].

[13] The method for treating a cancer according to [12], including administering, to a subject in need of treatment of leukemia, the activity enhancer for an anticancer agent according to any one of [1] to [5] or the pharmaceutical composition according to [8], and an anticancer agent against leukemia.

[14] Use of the D-form amino acid residue-containing FNIII14 polypeptide in the manufacture of the activity enhancer for an anticancer agent according to any one of [1] to [7] or the pharmaceutical composition for treatment of a cancer according to [8] or [9].

[15] The activity enhancer for an anticancer agent according to any one of [1] to [7] or the pharmaceutical composition according to any one of [8] or [9], which is used for a method for treating a cancer.

Advantageous Effects of Invention

According to the invention, an activity enhancer for an anticancer agent capable of enhancing the activity of an anticancer agent, and an anticancer composition that includes the activity enhancer, can be provided.

MODES FOR CARRYING OUT INVENTION

Figure 1:
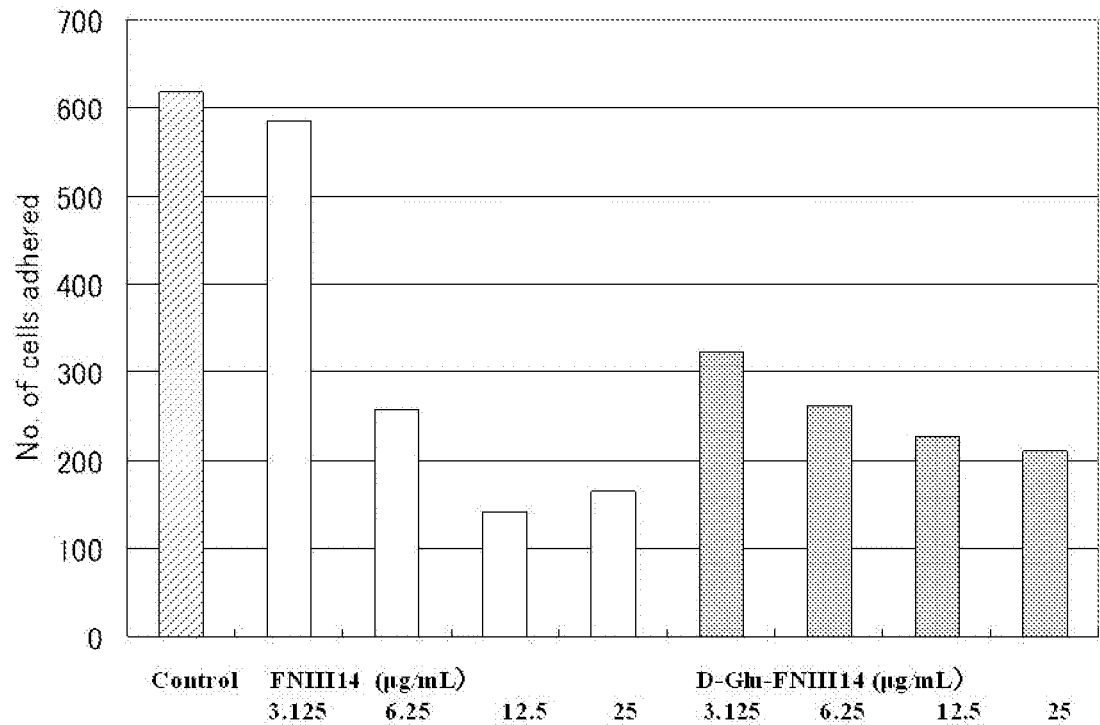
FIG. 1 is a graph showing the cell adhesion inhibitory activity of the polypeptide according to Example 1 of the invention.

An activity enhancer for an anticancer agent according to the invention (hereinafter sometimes referred to simply as "activity enhancer") is an activity enhancer for an anticancer agent that includes, as an active ingredient, a D-form amino acid residue-containing FNIII14 polypeptide, the D-form amino acid residue-containing FNIII14 polypeptide being a polypeptide FNIII14 represented by SEQ ID NO: 1 in which at least one of amino acid residues at positions 1 to 13 is a D-form amino acid residue.

A pharmaceutical composition for treatment of a cancer according to the invention is a composition that includes the activity enhancer described above and an anticancer agent.

A polypeptide according to the invention is either one of the following polypeptides:

(1) a polypeptide represented by SEQ ID NO: 1 in which at least one of the amino acid residues at positions 1 to 13 is a D-form amino acid residue; or (2) a polypeptide which is a multimer, of which the constituent unit is the polypeptide (1).

In the invention, the specific D-form amino acid residue-containing FNIII14 polypeptide that is a FNIII14 polypeptide represented by SEQ ID NO: 1 in which at least one of amino acid residues at the N-terminal side is a D-form amino acid residue, exhibits excellent stability in serum and can synergistically enhance the anticancer activity of an anticancer agent.

Thus, the effect of an anticancer agent can be enhanced by using the polypeptide in combination with the anticancer agent; further, both of the dose of the D-form amino acid residue-containing FNIII14 polypeptide and the dose of the anticancer agent combined therewith can be decreased, and risk to patients can be lowered.

The scope of the term "step" as used herein includes not only a discrete step, but also a step that cannot be clearly distinguished from another step as long as the expected effect of the step of interest is achieved.

In addition, any numerical range expressed herein using "to" refers to a range including the numerical values before and after "to" as the minimum and maximum values, respectively.

In a case in which the amount of a component that may be included in the composition is indicated in the invention, when there are plural substances corresponding to the component in the composition, the indicated amount means the total amount of the plural substances present in the composition, unless specifically stated otherwise.

In the invention, amino acid residues in an amino acid sequence that constitutes a polypeptide are sometimes represented by one-letter codes (such as "G" for a glycine residue) or three-letter codes (such as "Gly" for a glycine residue) known in the art.

The invention is described below.

The D-form amino acid residue-containing FNIII14 polypeptide in the invention is a D-form amino acid residue-containing FNIII14 polypeptide that is a FNIII14 represented by SEQ ID NO: 1 in which at least one of amino acid residues at positions 1 to 13 is a D-form amino acid residue.

The polypeptide FNIII14 represented by SEQ ID NO: 1 according to the invention is a sequence derived from the 14th fibronectin III-like repetitive sequence (FNIII) of human fibronectin.

In the sequence represented by SEQ ID NO: 1, the other portion than the amino acid residues at positions 1 to 13 is an active sequence YTIYVIAL (SEQ ID NO: 3). Thus, at least one of the amino acid residues at the N-terminal side, other than the active sequence, should be a D-form amino acid residue in the invention. Such a D-form amino acid residue-containing FNIII14 polypeptide can improve the stability of FNIII14 in serum and can more strongly enhance the anticancer agent activity of an anticancer agent that is used in combination with the polypeptide. It is already known that FNIII14 is a polypeptide consisting of 21 amino acid residues represented by TEATITGLEPGTEYTIYVIAL (SEQ ID NO: 1), and that, from among the 21 amino acid residues, eight amino acid residues (YTIYVIAL (SEQ ID NO: 3)) starting from tyrosine (Y) at position 14 constitute an active center.

The number of D-form amino acid residues that can be included at amino acid residue positions 1 to 13 in the FNIII14 represented by SEQ ID NO: 1 is preferably from 1 to 6, more preferably 1 to 3, and still more preferably 1, from the viewpoints such as the stability in blood, the improvement of the physiological activity of the FNIII14, and a synergistic effect with an anticancer agent. In addition, the positions of amino acid residues substitutable with D-form amino acid residues may be any positions, and are preferably positions 1 to 10, more preferably positions 1 to 6, and still more preferably position 2, in the polypeptide represented by SEQ ID NO: 1.

Furthermore, the combination of the number and positions of D-form amino acid residues in the D-form amino acid residue-containing FNIII14 polypeptide may be a combination of a preferable number of D-form amino acid residues described above and preferable positions of D-form amino acid residues described above.

Examples of preferable embodiments of the D-form amino acid residue-containing FNIII14 polypeptide include the following polypeptides:

(1) a polypeptide containing from one to six D-form amino acid residues at any position or positions selected from positions 1 to 10 of the polypeptide represented by SEQ ID NO: 1;

(2) a polypeptide containing from one to three D-form amino acid residues at any position or positions selected from positions 1 to 6 of the polypeptide represented by SEQ ID NO: 1; and (3) a polypeptide containing one D-form amino acid residue at any of positions 1 to 10 of the polypeptide represented by SEQ ID NO: 1.

From the viewpoint of the effect in terms of enhancing the activity of an anticancer agent, the D-form amino acid residue-containing FNIII14 polypeptide is more preferably a D-form glutamic acid-containing polypeptide that contains one D-form glutamic acid residue, the one D-form glutamic acid residue corresponding to an amino acid residue at position 2 of the polypeptide represented by SEQ ID NO: 5.

The D-form amino acid residue-containing FNIII14 polypeptide may include other modifications for the purpose of, for example, improvement in its physiological activity, as long as the polypeptide retains the active sequence and contains at least one D-form amino acid residue.

For example, the D-form amino acid residue-containing FNIII14 polypeptide may be a modified D-form amino acid residue-containing FNIII14 polypeptide in which at least one amino acid residue of the polypeptide FNIII14 represented by SEQ ID NO: 1 is replaced by another standard amino acid (standard amino acid meaning an amino acid encoded by a gene) or an abnormal amino acid (the scope of which includes nonstandard amino acids found in nature and artificially-prepared sterically-constrained amino acids) as typified by D-form amino acids other than the above-described D-form amino acid residues. The D-form amino acid residue-containing FNIII14 polypeptide may alternatively be a multivalent peptide obtained by binding these plural active peptides on a template molecule having plural functional groups by utilizing covalent bonds such as peptide bonds or disulfide bonds.

Here, examples of the nonstandard amino acids included in abnormal amino acids include D-methylleucine, N-hydroxy-L-alanine, and β-hydroxyleucine. Examples of the sterically-constrained amino acids include α,α-disubstituted amino acids such as 2-aminoisobutyric acid, β-methylphenylalanine, and cyclopropane amino acid.

Examples of the template molecule include a peptide containing one functional group, or two or more functional groups, such as an amino group, a carboxyl group, a thiol group, or a maleimide group. These template molecules are able to bind to one molecule of, or plural molecules of, the above-described D-form amino acid residue-containing FNIII13 peptide via a functional group on the polypeptide. This binding is expected to provide, for example, further improvement of the stability in serum of the D-form amino acid residue-containing FNIII13 polypeptide, and further improvement of handleability. The functional group on the polypeptide can be produced on the polypeptide chain using a known means for, for example, cleaving a bond portion such as a peptide bond or a disulfide bond in the polypeptides.

In addition, examples of modification for providing stability in serum include acetylation of an amino acid residue at position 1, namely, a threonine residue.

The D-form amino acid residue-containing FNIII14 polypeptide of the invention can be synthesized by, for example, a chemical synthesis method such as a solid-phase synthesis method, or a synthesis method using a gene recombination technique in which the polypeptide is synthesized by inserting a DNA sequence encoding the amino acid sequence into a plasmid vector and transforming a microorganism such as *E. coli* with the plasmid vector. The chemical synthesis is most commonly carried out using a solid-phase peptide synthesis method. This method is described below as an example of the synthesis method; however, the synthesis method is not limited thereto.

A protected amino acid, specific examples of which include 9-fluorenylmethyloxycarbonyl (Fmoc)-Leu-OH, Fmoc-Ala-OH, Fmoc-Ile-OH, Fmoc-Val-OH, Fmoc-Thr (Bzl)-OH, Fmoc-Tyr(tBu)-OH, Fmoc-Glu(OBzl)-OH, Fmoc-Gly-OH, and Fmoc-Pro-OHOn, is introduced to a polystyrene resin having a polyethylene glycol chain.

A method employed for the introduction is, for example, as follows. The amino acid (1 mmol) is dissolved in an N,N-dimethylformamide (DMF) solution that contains 1 mmol of 2-(1-H-benzotriazol-1-yl)-1,1,3,3-tetramethyluronium (HBTU) and 1 mmol of N-hydroxybenzotriazole (HOBt), and thereafter mixed with polystyrene resin. After 30 minutes, the insoluble resin is washed with DMF and then the resin is suspended in a 20% piperidine solution in DMF (removal of the Fmoc group). Thereafter, these operations are repeated until a desired peptide chain is obtained. In order to cut away the desired peptide from the polystyrene resin and to remove a protective group such as a benzyl group, the peptide is allowed to react for 1 hour in trifluoroacetic acid. The resulting crude product is purified with HPLC, whereby a uniform peptide can be obtained. The structure of the synthesized peptide can be confirmed using a time-of-flight molecular mass spectrometer.

In the synthesis method using a gene recombination technique, the cell adhesion inhibitory peptide can be produced by synthesizing a gene encoding the cell adhesion inhibitory peptide using, for example, a DNA synthesis apparatus (a DNA synthesizer), incorporating the gene into a known plasmid vector, and introducing the resultant recombinant vector into a host microorganism so as to create a transformant. The plasmid vector used in this method is not particularly limited as long as the vector is an expression vector for producing a protein. The host is not limited to a microorganism, and eukaryotic cells, such as COS cells, may be employed.

Methods for producing the D-form amino acid residue-containing FNIII14 polypeptide are not particularly limited, and known polypeptide synthesis methods may be applied. Any known method that includes a step of applying a D-form at a specific amino acid residue in a polypeptide synthesis process may be employed.

An example of a method for purifying the obtained crude peptide is a method including separating and purifying a desired peptide using any of various types of ion exchange chromatography, gel filtration chromatography, or high-performance liquid chromatography using a reverse-phase column.

The D-form amino acid residue-containing FNIII14 polypeptide can be multimerized, for example, trimerized or dendrimerized. A multimer obtained by the multimerization, of which the constituent unit is the D-form amino acid residue-containing FNIII14 polypeptide described above, exhibits further improved stability in serum and more effectively enhances the activity of an anticancer agent, thereby providing excellent therapeutic effect against a cancer.

A multimer of the D-form amino acid residue-containing FNIII14 can be obtained using a known multimerization method.

For example, a method for producing a trimer includes dissolving a prepared monomer peptide FNIII14 in DMSO and PBS, and then dropwise adding a DMSO solution of TMEA (Tris[2-maleimidoethyl]amine) thereto, to obtain a trimer. The purity and structure of the obtained product can be checked using HPLC and MALDI-TOF MS analysis.

In the case in which a solid-phase synthesis method is employed for synthesizing a monomer peptide, a method for producing a dendrimer (a dendritic structure) may include preparing a peptide having BMPA (N-β-maleimidopropionic acid) at a terminal thereof, dissolving the peptide in DMSO and PBS, and dropwise adding thereto a DMSO solution of a cyclic peptide that contains from 3 to 6 cysteine residues. Other than the above, a building brick having an appropriate functional group may be introduced to a terminal of the peptide, and a dendrimer can be synthesized using the peptide. In the synthesis, an amino group and a carboxyl group, a thiol group and a maleimide group, or a combination of thiol groups, may be used. The purity and structure of the obtained product can be checked using HPLC and MALDI-TOF MS analysis.

Trimers and dendrimers can also be obtained using other production methods than those described above. Therefore, the production methods are not limited to the methods described above.

The scope of the multimer of the D-form amino acid residue-containing FNIII14 also includes a multimer formed by any combination of the following constituent units (1) to (3) or a multimer formed by one type selected from the following constituents units (1) to (3):

(1) a constituent unit formed of a polypeptide having from one to six D-form amino acid residues at any position or positions selected from positions 1 to 10 of the polypeptide represented by SEQ ID NO: 1;

(2) a constituent unit formed of a polypeptide having from one to three D-form amino acid residues at any position or positions selected from positions 1 to 6 of the polypeptide represented by SEQ ID NO: 1; and (3) a constituent unit composed of a polypeptide having one D-form amino acid residue at any of positions 1 to 10 of the polypeptide represented by SEQ ID NO: 1;

In the multimer of the D-form amino acid residue-containing FNIII14, all constituent units thereof preferably have the same number of D-form amino acid residue(s) at the same position(s).

The types of cancers that can be treated by the cancer treatment according to the invention are not particularly limited. Examples thereof include all kinds of leukemia, such as acute leukemia, chronic myeloid leukemia, and lymphocytic leukemia, cancer of the head, oral/tongue cancer, pharyngeal cancer, thyroid cancer, lung cancer, breast cancer, esophageal cancer, stomach cancer, colon cancer, liver cancer, gallbladder cancer, pancreatic cancer, kidney cancer, bladder cancer, prostate cancer, cervical cancer, corpus uteri cancer, ovarian cancer, skin cancer, bone cancer, and soft tissue cancer; however, the types of cancers are not limited to these organs or tissues.

The anticancer agent to be strengthened by the D-form amino acid residue-containing FNIII14 polypeptide may be any anticancer agent having a therapeutic effect against a solid cancer or leukemia. Examples thereof include the following: alkylating agents such as nitrogen mustard, cyclophosphamide, ifosfamide, melphalan, busulfan, improsulfan tosylate, mitobronitol, carboquone, thiotepa, ranimustine, and nimustine; antimetabolites such as methotrexate, 6-mercaptopurine riboside, mercaptopurine, 5-fluorouracil (5-FU), tegafur, UFT, doxifluridine, carmofur, cytarabine, cytarabine ocfosfate, elacytarabine, and enocitabine; anticancerous antibiotics such as actinomycin D, doxorubicin, daunorubicin, neocarzinostatin, bleomycin, peplomycin, mitomycin C, aclarubicin, pirarubicin, epirubicin, zinostatin stimalamer, and idarubicin; plant alkaloid-based anticancer agents such as vincristine, vinblastine, vindesin, etoposide, irinotecan, sobuzoxane, docetaxel, and paclitaxel; platinum complex compounds such as cisplatin, carboplatin, and nedaplatin; and other anticancer agents not included in the above classes, such as mitoxantrone, L-asparaginase, procarbazine, dacarbazine, hydroxycarbamide, pentostatin, and tretinoin.

Among them, anticancer agents having an anticancer activity against leukemia, such as cytarabine (AraC), elacytarabine, and enocitabine, are preferable from the viewpoint of the enhancing effect exerted by the D-form amino acid residue-containing FNIII14 polypeptide. By combining the D-form amino acid residue-containing FNIII14 polypeptide with these anticancer agents having an anticancer activity against leukemia, in particular, slightly-surviving residual cancer in bone marrow, which is a cause of recurrence of AML, can more likely be eradicated.

To patients, the activity enhancer for an anticancer agent according to the invention may be administered alone or in the form of a pharmaceutical composition for treatment of a cancer in which the activity enhancer is combined with one type of the above-described anticancer agent. In a case in which clinical use of plural anticancer agents against a specific cancer is approved, an anticancer composition or anticancer compositions, in which those anticancer agents are combined with the activity enhancer of the invention, may be used. Further, in a case in which plural anticancer agents are administered against two or more types of cancers that are different from each other, the anticancer agents may be combined with the activity enhancer of the invention and used.

In a case in which the activity enhancer for an anticancer agent is used together with the anticancer agent, the therapy with the anticancer agent and the activity enhancer may be carried out in combination with another therapeutic method against cancer, whereby more effective therapeutic effects can be expected as compared to a case in which each of the therapeutic methods is carried out singly. For example, in a case in which the therapy with the anticancer agent and the activity enhancer is carried out with surgical resection, the chemotherapy may be continued regardless of whether before or after the operation. The therapy with the anticancer agent and the activity enhancer may be carried out in combination with radiation therapy.

The dose of the activity enhancer to be combined with the anticancer agent may be selected, as appropriate, in accordance with the age, symptoms, and the like of the patient, and the dose may be any dose with which the anticancer activity of the anticancer agent is enhanced, without particular limitation. In practice, the dose may vary widely, in accordance with a proper dose of the anticancer agent. Usually, the amount of the activity enhancer to be taken at one time (unit dosage amount) is from 0.01 mg to 10 g/kg body weight.

The dose of the anticancer agent varies with the type of the anticancer agent to be used. For example, the dose is preferably in a range of from 0.001 μg to 0.5 mg/kg body weight (intravenous administration) in the case of actinomycin D, from 0.05 mg to 600 mg/m$^2$ body surface area (intravenous administration) in the case of doxorubicin, from 1 ng to 0.5 mg/kg body weight (intravenous administration) in the case of vincristine, from 1 mg to 125 mg/kg body weight (intravenous administration) or from 2.5 mg to 3 g/kg body weight in the case of 5-fluorouracil, and from 0.05 mg to 5 g/m$^2$ body surface area (intravenous administration) in the case of cyclophosphamide.

The activity enhancer may be administered to a patient through any administration route, and intravenous administration, local administration to a diseased area, and oral administration are preferable. In particular, intravenous administration and local administration to a diseased area are more preferable.

It is preferable that the activity enhancer and an anticancer agent are administered as a single mixed formulation (an anticancer composition) to a patient after the activity enhancer and the anticancer agent are mixed together. However, similar therapeutic effects can be expected also when the activity enhancer and the anticancer agent are administered through respectively different administration routes (for example, intravenous administration of the activity enhancer and oral administration of the anticancer agent).

In a case in which the activity enhancer and an anticancer agent are separately administrated, the dose or the like of each of the activity enhancer and the anticancer agent may be set in accordance with the type of the anticancer agent to be administered, the condition of the patient, and the like. The activity enhancer may be administered before the administration of the anticancer agent or after the administration of the anticancer agent. However, the interval between the administration of the anticancer agent and the administration of the activity enhancer is preferably rather short. For example, the interval is preferably within about 1 hour.

In the administration, each of the activity enhancer and the anticancer agent may be individually administered, or administered in the form of a pharmaceutical composition for treatment of a cancer (an anticancer composition) that includes both of the activity enhance and the anticancer agent, and each of the activity enhancer and the anticancer agent or the pharmaceutical composition is preferably administered in the form of a formulation that optionally includes freely-selected carriers and additives such as pharmaceutically acceptable carriers, diluents, excipients, and stabilizers. Pharmaceutically acceptable carriers and additives used for this purpose are well known to those skilled in the art.

Pharmaceutically acceptable carriers and additives to be used in the invention may be selected, as appropriate, in accordance with the administration route of the activity enhancer for an anticancer agent or the anticancer composition. Examples of the carriers and additives include water, pharmaceutically acceptable organic solvents, collagen, polyvinyl alcohol, polyvinyl pyrrolidone, carboxy vinyl polymer, sodium carboxymethylcellulose, sodium polyacrylate, sodium alginate, water-soluble dextran, sodium carboxymethyl starch, pectin, methyl cellulose, ethyl cellulose, xanthan gum, gum arabic, casein, gelatin, agar, diglycerin, propylene glycol, polyethylene glycol, vaseline, paraffin, stearyl alcohol, stearic acid, human serum albumin (HAS), mannitol, sorbitol, lactose, and surfactants that are acceptable as pharmaceutical additives. The additives to be used may be selected, as appropriate, from those described above, in accordance with the dosage form. However, the additives are not limited to those described above.

An anticancer therapeutic agent set of the invention includes a first container section in which the activity enhancer described above is contained and a second container section in which an anticancer agent is contained.

The container sections in the kit may be, without particular limitation, any container sections having shapes effective for allowing the respective agents to be independently present without being mixed together. Each container section may be, for example, a container, an individually packaged form, or the like. The container sections may alternatively have a form of independently partitioned regions of a single sheet.

When using the anticancer therapeutic agent set, each of the agents may be individually administered, or, alternatively, the activity enhancer and the anticancer agent may be taken out from the respective container sections and mixed together, when needed, to prepare a formulation (an anticancer composition). Regarding the types, administration routes, doses, and the like of the activity enhancer and the anticancer agent, the explanations thereof described above shall apply as they are.

The invention also encompasses a method for treating a cancer, the method including administrating the activity enhancer for an anticancer agent according to the invention or the anticancer composition according to the invention to a patient suspected to have a tumor or a cancer, a patient already suffering from a tumor or a cancer, or a patient in need of treatment of a tumor or a cancer (an administration step). As used herein, the term "treatment" encompasses any improvement of symptoms; suppression of enlargement of a lesion or shrinkage of a lesion, reduction of metastasis rate, or cessation of metastasis is also encompassed by this term as long as such a change can be confirmed.

In the administration step, the activity enhancer and an anticancer agent are administered to the same individual, and there is no limitation on the order, form, or the like of administration. For example, the administration step may include each of a step of administering the activity enhancer and a step of administering an anticancer agent. The administration step may alternatively be a step of simultaneously administering the activity enhancer and an anticancer agent, or a step of administering an anticancer composition containing the activity enhancer and an anticancer agent.

Regarding the types, administration routes, doses, and the like of the activity enhancer for an anticancer agent and the anticancer agent to be used in the present method for treating a cancer, the explanations thereof described above shall apply, as they are, to the present method for treating a cancer.

The invention also encompasses use of the D-form amino acid residue-containing FNIII14 polypeptide in the manufacture of the activity enhancer for an anticancer agent or the pharmaceutical composition for treatment of a cancer. By using the polypeptide together with an anticancer agent, an activity enhancer for an anticancer agent or a pharmaceutical composition for treatment of a cancer, each of which can enhance the effect of the anticancer agent, can be provided.

In the following, the invention is described in more detail with reference to examples. However, the invention is not limited to these examples. Further, "%" represents percent by mass unless otherwise specified.

EXAMPLES

Example 1

Preparation of Polypeptides

Synthesis of the polypeptide FNIII14 (SEQ ID NO: 1) used in the examination was synthesized by Sawady Technology Co., Ltd., Tokyo at our request, using a peptide synthesizer (Multiple Peptide Synthesizer SYRO II, manufactured by Multi SynTec GmbH). The sequence of the synthesized peptide was checked using a peptide sequencer (Model 476A, manufactured by Applied Biosystems Co., Ltd).

In addition, a D-Glu-FNIII14 T-[D-Glu]-ATIT-GLEPGTEYTIYVIAL (SEQ ID NO: 5)), in which the amino acid residue at position 2 in the sequence of FNIII14 is a D-form glutamic acid, was synthesized in the following manner:

Onto a polystyrene resin having a polyethylene glycol chain, 9-fluorenylmethyloxycarbonyl (Fmoc)-Leu-OH was introduced first. Specifically, Fmoc-Leu-OH (1 mmol) was dissolved in an N,N-dimethylformamide (DMF) solution containing 1 mmol of 2-(1-H-benzotriazole-1-yl)-1,1,3,3-tetramethyluronium (HBTU) and 1 mmol of N-hydroxybenzotriazole (HOBt), and then the solution was mixed with the polystyrene resin. After 30 minutes, the insoluble resin was washed with DMF, and then the resin was suspended in a 20% piperidine solution in DMF (removal of the Fmoc group). Then, Fmoc-Ala-OH, Fmoc-Ile-OH, Fmoc-Val-OH, Fmoc-Tyr(tBu)-OH, Fmoc-Ile-OH, Fmoc-Thr(Bzl)-OH, Fmoc-Tyr(tBu)-OH, Fmoc-Glu(OBzl)-OH, Fmoc-Thr(Bzl)-OH, Fmoc-Gly-OH, Fmoc-Pro-OH, Fmoc-Glu(OBzl)-OH, Fmoc-Leu-OH, Fmoc-Gly-OH, Fmoc-Thr(Bzl)-OH, Fmoc-Ile-OH, Fmoc-Thr(Bzl)-OH, Fmoc-Ala-OH, Fmoc-D-Glu(OBzl)-OH, and Fmoc-Thr(Bzl)-OH were introduced, employing the same operations. The obtained peptide was cleaved away from the resin, and allowed to react for 1 hour in trifluoroacetic acid in order to remove protective groups such as a Bzl group (benzyl group). The resulting crude product was purified using HPLC, whereby a uniform peptide was obtained. In addition, the structure of the synthesized peptide was checked using a time-of-flight molecular mass spectrometer.

The process employed for synthesizing Ace-FNIII14 was as follows.

Onto a polystyrene resin having a polyethylene glycol chain, 9-fluorenylmethyloxycarbonyl (Fmoc)-Leu-OH was introduced first. Specifically, Fmoc-Leu-OH (1 mmol) was dissolved in an N,N,-dimethylformamide (DMF) solution containing 1 mmol of 2-(1-H-benzotriazole-1-yl)-1,1,3,3-tetramethyluronium (HBTU) and 1 mmol of N-hydroxybenzotriazole (HOBt), and then the solution was mixed with the polystyrene resin. After 30 minutes, the insoluble resin was washed with DMF. Thereafter, the resin was suspended in a 20% piperidine solution in DMF, to remove the Fmoc group. Then, Fmoc-Ala-OH, Fmoc-Ile-OH, Fmoc-Val-OH, Fmoc-Tyr(tBu)-OH, Fmoc-Ile-OH, Fmoc-Thr(Bzl)-OH, Fmoc-Tyr(tBu)-OH, Fmoc-Glu(OBzl)-OH, Fmoc-Thr(Bzl)-OH, Fmoc-Gly-OH, Fmoc-Pro-OH, Fmoc-Glu(OBzl)-OH, Fmoc-Leu-OH, Fmoc-Gly-OH, Fmoc-Thr(Bzl)-OH, Fmoc- Ile-OH, Fmoc-Thr(Bzl)-OH, Fmoc-Ala-OH, Fmoc-Glu(OBzl)-OH, and Fmoc-Thr(Bzl)-OH were introduced, employing the same operations. The insoluble resin was suspended in a 20% piperidine solution in DMF, to remove the Fmoc group. Separately, 5 mmol each of acetic acid, dicyclohexylcarbodiimide, and 1-hydroxybenzotriazole were allowed to react in dichloromethane for 30 minutes, and the filtrate was added to the insoluble resin. After 30 minutes, the insoluble resin was washed with DMF. The insoluble resin was allowed to react for 1 hour in trifluoroacetic acid in order to cleave away the desired peptide from the resin and to remove protective groups such as a Bzl group. The resulting crude product was purified using HPLC, whereby a uniform peptide was obtained. The structure of the synthesized peptide was checked using a time-of-flight molecular mass spectrometer.

The process employed for synthesizing Methylated-FNIII14 ([N-Me-Glu]$^2$-FNIII14) was as follows.

On a polystyrene resin having a polyethylene glycol chain, 9-fluorenylmethyloxycarbonyl (Fmoc)-Leu-OH was introduced first. Specifically, Fmoc-Leu-OH (1 mmol) was dissolved in an N,N,-dimethylformamide (DMF) solution containing 1 mmol of 2-(1-H-benzotriazole-1-yl)-1,1,3,3-tetramethyluronium (HBTU) and 1 mmol of N-hydroxybenzotriazole (HOBt), and then the solution was mixed with the polystyrene resin. After 30 minutes, the insoluble resin was washed with DMF. Then, the resin was suspended in a 20% piperidine solution in DMF (removal of the Fmoc group). Then, Fmoc-Ala-OH, Fmoc-Ile-OH, Fmoc-Val-OH, Fmoc-Tyr(tBu)-OH, Fmoc-Ile-OH, Fmoc-Thr(Bzl)-OH, Fmoc-Tyr(tBu)-OH, Fmoc-Glu(OBzl)-OH, Fmoc-Thr(Bzl)-OH, Fmoc-Gly-OH, Fmoc-Pro-OH, Fmoc-Glu(OBzl)-OH, Fmoc-Leu-OH, Fmoc-Gly-OH, Fmoc-Thr(Bzl)-OH, Fmoc-Ile-OH, Fmoc-Thr(Bzl)-OH, Fmoc-Ala-OH, Fmoc-N-Me-Glu(OBzl)-OH, and Fmoc-Thr(Bzl)-OH were introduced, employing the same operations. The insoluble resin was allowed to react for 1 hour in trifluoroacetic acid in order to cleave the desired peptide away from the resin and to remove protective groups such as a Bzl group. The resulting crude product was purified using HPLC, whereby a uniform peptide was obtained. The structure of the synthesized peptide was checked using a time-of-flight molecular mass spectrometer.

<Evaluation> Cell Adhesion Inhibitory Activity

A 96-well cell culture plate (manufactured by Corning Inc.) was coated with human-derived plasma fibronectin (hereinafter referred to as "FN", prepared by the method of Fukai, et al (Fukai et al., J. Biol. Chem., 266, 8807, 1991)) having a concentration of 0.5 μg/mL. A375SM cells ($2\times10^4$ cells) were suspended in a serum-free medium at a cell concentration of $2\times10^5$ cell/ml, and a peptide solution containing D-Glu-FNIII14 or FNIII14 (dissolved in phosphate buffered saline) was mixed with the cell suspension to give a final concentration of from 3.125 to 25 μg/ml. The resultant mixture was inoculated into wells of the plate. As a control, peptide-free PBS alone was added to wells in a similar manner. The medium used was a DMEM (manufactured by Gibco BRL Co., Ltd).

The plate was subjected to culturing at 37° C. for 1 hour in a 5 v/v % $CO_2$ atmosphere. Then, 100 μL of a PBS (-) solution containing 4% of formalin and 5% of sucrose was gently added to the wells, and left to stand at room temperature for 1 hour, whereby the cells were immobilized. After the immobilization, non-adhered cells in the PBS were removed by washing, and the number of cells observed in predetermined four fields was counted, and taken as the number of adhered cells. The results are shown in FIG. 1.

As shown in FIG. 1, D-Glu-FNIII14 was found to have the same level of adhesion inhibitory activity as that of FNIII14. This indicates that the FNIII14 activity was not decreased in D-Glu-FNIII14 even though a D-form amino acid was contained at the N-terminal side.

Example 2

Preparation of Trimer and Dendrimer (1) Method for Preparing Trimer (Trimeric Ac-FNIII14)

A monomeric peptide FNIII14 prepared according to the above-described method was dissolved in DMSO and PBS, and then a DMSO solution of TMEA (Tris[2-maleimidoethyl]amine) was dropwise added thereto, whereby a trimer was obtained.

The structure of the synthesized peptide was analyzed using a time-of-flight molecular mass spectrometer, thereby confirming that a trimer was obtained.

Using a similar procedure, a trimer of D-Glu-FNIII14 can be obtained from a monomer of D-Glu-FNIII14.

(2) Method for Producing Dendrimer

A peptide having BMPA (N-β-maleimidopropionic acid) at a terminal thereof was prepared using the solid-phase method for synthesizing a monomeric peptide FNIII14. The peptide was dissolved in DMSO and PBS, and a DMSO solution of a cyclic peptide containing six cysteine residues was dropwise added thereto, whereby a dendrimer was obtained.

The structure of the synthesized peptide was analyzed by a time-of-flight molecular mass spectrometer, thereby confirming that a dendrimer was obtained.

Using a similar procedure, a multimer (dendrimer) of D-Glu-FNIII14 can be obtained from a monomer of D-Glu-FNIII14.

Example 3

Evaluation of Stability of Peptide in Human Serum

Figure 2A:
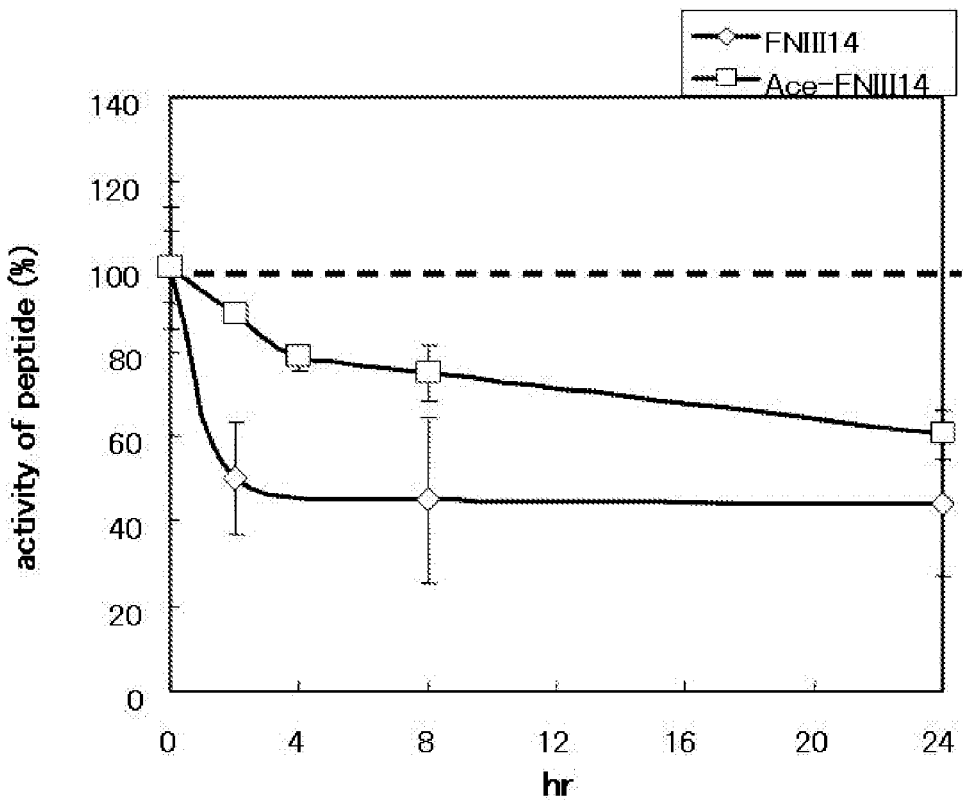
FIG. 2A is a graph showing the stability in serum of the polypeptide according to Example 3 of the invention.
Figure 2B:
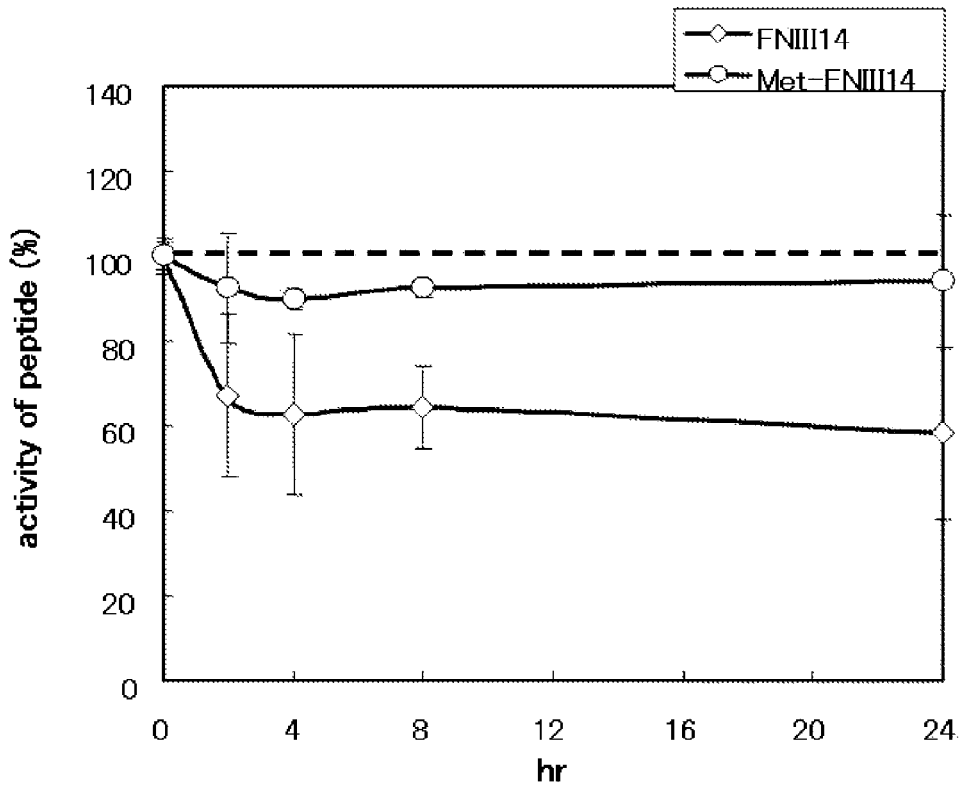
FIG. 2B is a graph showing the stability in serum of the polypeptide according to Example 3 of the invention.
Figure 2C:
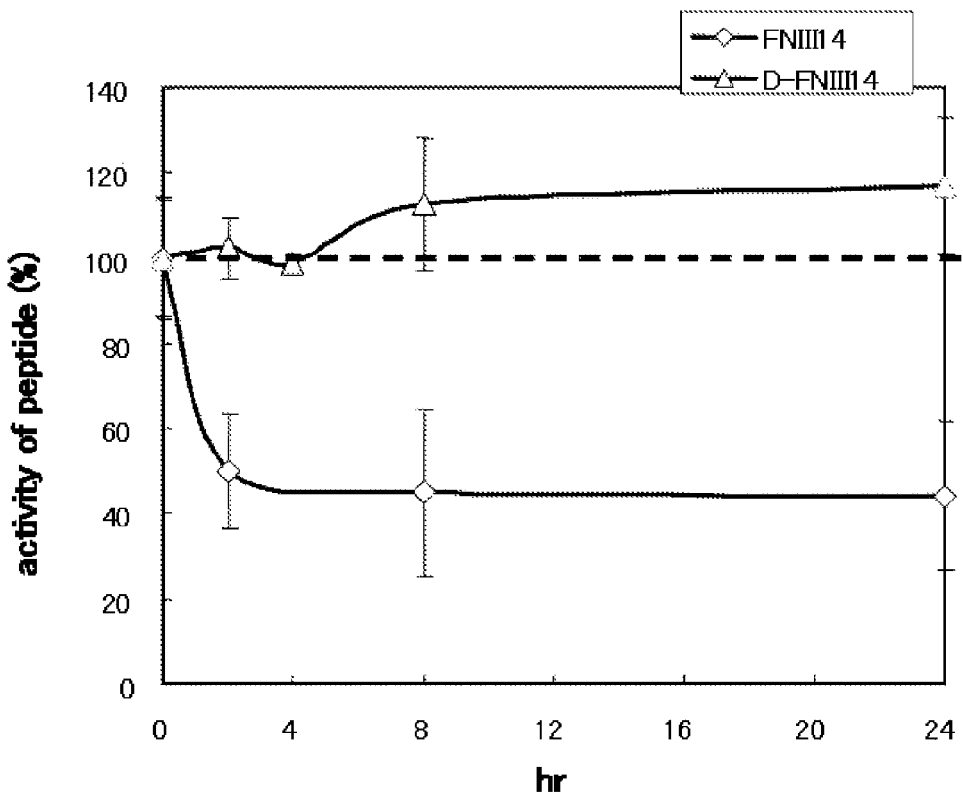
FIG. 2C is a graph showing the stability in serum of the polypeptide according to Example 3 of the invention.
Figure 2D:
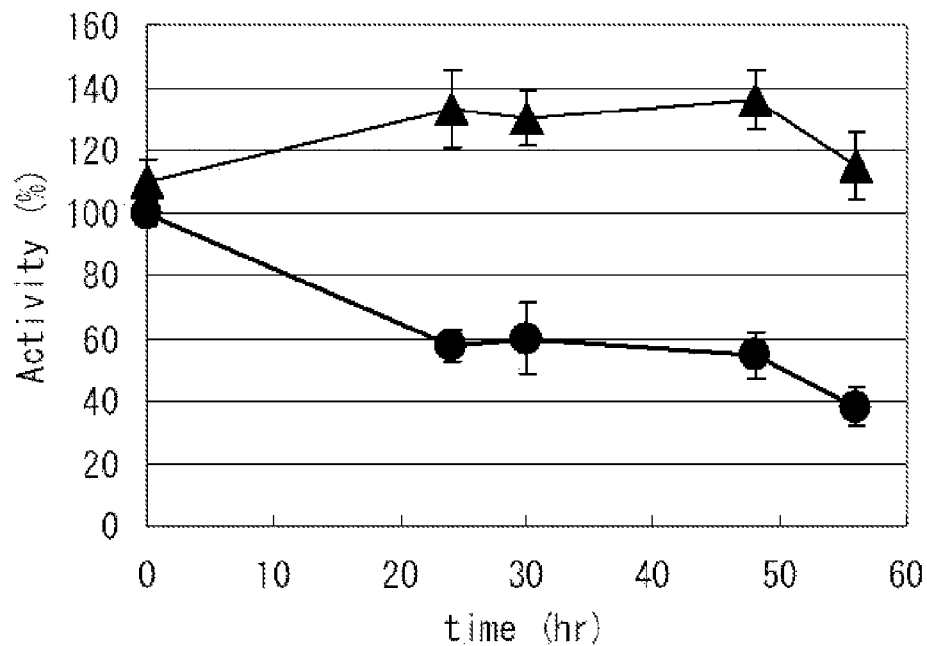
FIG. 2D is a graph showing the stability in serum of the polypeptide according to Example 3 of the invention.

FNIII14 (500 μg/mL), each of the modified peptides (500 μg/mL), or a solution thereof was incubated in human serum (final concentration 90%; 0.01% of sodium azide as a preservative having been added thereto) under a condition of 37° C. and 5% $CO_2$ for determined periods in a range of from 0 to 56 hours. Thereafter, each sample was diluted with DMEM (-) such that the peptide concentration in each well would be 25 μg/mL, and was inoculated onto a 96-well tissue culture plate together with A375SM cells prepared at $1.5\times10^4$/well, the 96-well tissue culture plate having been coated with 0.5 μg/mL of FN. After the plate was subjected to culturing for a certain time, 100 ml of a PBS (-) solution containing 4% of formalin and 5% of sucrose was gently added to wells, and left to stand at room temperature for 1 hour, whereby the cells were immobilized. After the immobilization, the number of cells observed in predetermined four fields was counted and taken as the total number of cells. Non-adhered cells were removed by washing with a PBS (-) solution three times, and then the number of adhered cells in the same four fields as those mentioned above was counted under a microscope. Assuming that the adhesion inhibitory activity of FNIII14 that was not subjected to the treatment with serum was 100, the ratio of the residual adhesion inhibitory activity of FNIII14 or the modified peptide remaining after the serum treatment was evaluated in terms of percentage. The results are shown in FIGS. 2A to 2D. In FIGS. 2A to 2C, white diamonds represent the results obtained using FNIII14, white squares represent the results obtained using Ace-FNIII14, white circles represent the results obtained using Met-FNIII14, and white triangles represent the results obtained using D-FNIII14. In FIG. 2D, black circles represent the activity of FNIII14, and black triangles represent the activity of D-Glu-FNIII14.

As shown in FIG. 2A, FNIII14 rapidly lost its activity within 2 hours, and the activity thereof became about 60% after 20 hours. In contrast, Ace-FNIII14 (see FIG. 2B) and Met-FNIII14 (see FIG. 2C) were more stabilized than FNIII14. D-Glu-FNIII14 exhibited resistance to decomposition by aminopeptidase or the like in human serum. D-Glu-FNIII14 did not exhibit a decrease of its activity in the serum, and, rather, its activity was found to increase by 20% or more.

Human serum was used in the present bioassay. Since this peptide can avoid inhibitors in the blood, the activity thereof was over 100%. This suggests that, in order to maintain the concentration in blood for the purpose of treatment, intravenous injection at an interval of 1 day or longer is expected to be sufficient in the case of D-Glu-FNIII14 whereas intravenous injection at an interval of about 1 hour is necessary in the case of FNIII14. FIG. 2D illustrates long term stability over a period of 60 hours. Since D-Glu-FNIII14 exhibited decomposition tendency at or after 50 hours, it is understood that unnecessarily long retention in blood can be avoided. Due to the achievement of these properties, release control necessary in DDS technique is facilitated.

Example 4

Evaluation of Activity in Terms of Reinforcement of Anticancer Agent

A cell suspension (DMEM medium containing 1 mM of magnesium chloride and 20% of human serum) containing leukemia cell line U937 was inoculated onto a 96-well tissue culture plate that had been coated with 10 μg/mL of FN, at a cell concentration of $2.5 \times 10^4$ cells/well. To each well, FNIII14 or D-Glu-FNIII14 was added to have a concentration of 100 μg/mL, and the cells were cultured for 2 hours under a condition of 37° C. and 5% $CO_2$. Thereafter, cytarabine (AraC, Kyowa Hakko Co., Ltd.) was added at the respective concentrations of 0, $10^{-8}$M, $10^{-7}$M, $10^{-6}$M, and $10^{-5}$M, and the plate was subjected to culturing for 24 hours. Then, the number of viable cells was measured according to the WST method using a cell counting kit (Wako Pure Chemical Industries, Ltd.) (measurement wavelength: 450 nm, reference wavelength: 655 nm). Here, each of the culturing processes was carried out using RPMI 1640 to which human serum (a mixture of sera from four healthy volunteers) had been added to a concentration of 20%. The results are shown in FIG. 3.

Figure 3:
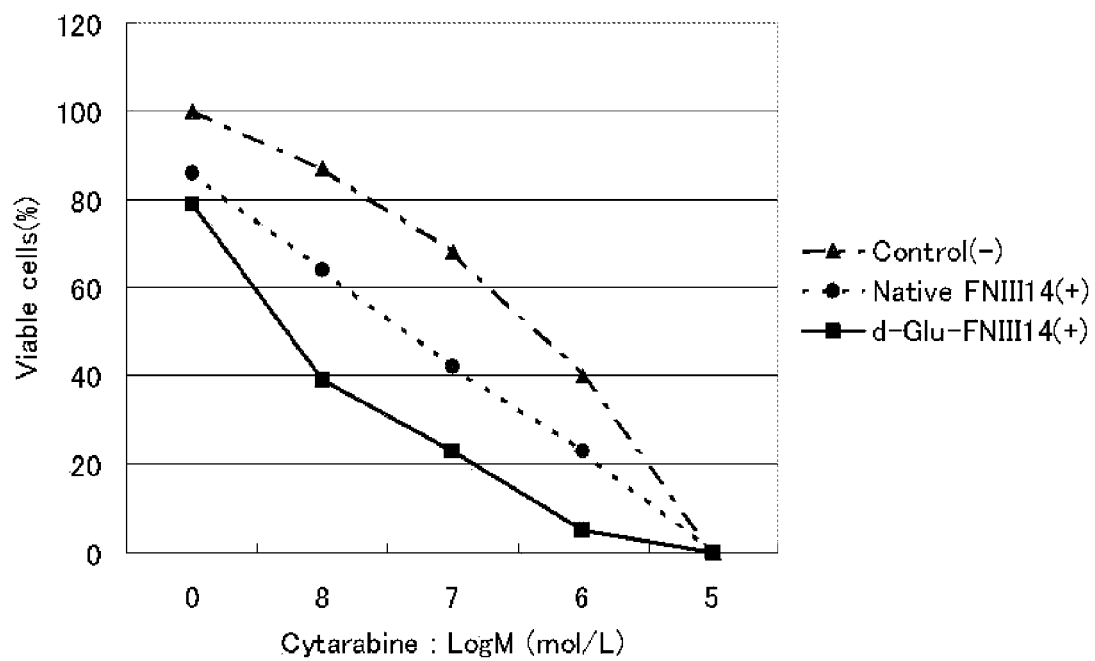
FIG. 3 is a graph showing an effect of the polypeptide according to Example 1 of the invention on the enhancement of activity of an anticancer agent against a leukemia cell line.

The results are shown in FIG. 3. As shown in FIG. 3, D-Glu-FNIII14 was found to have a superior effect on the reduction in the viable U937 cells in the presence of AraC, as compared to that of FNIII14. Moreover, the $IC_{50}$ of AraC in the presence of D-Glu-FNIII14 demonstrates an inhibitory effect that is about 100 times higher than that observed in the absence of peptide, and about 10 times higher than that observed in the presence of FNIII14.

Further, in FIG. 3, the combined use with D-Glu-FNIII14 formed a curve greatly arching out downward, which demonstrates a synergistic effect. In contrast, almost a straight line was observed in the case of FNIII14, which indicates no synergistic effect. A combination index, which is an indicator of synergistic effect, was calculated with respect to the synergistic effect between D-Glu-FNIII14 and Ara-C, according to a report of Drewinko, et al., (Drewinko, B., Green, C., and Loo, T. L. (1976) Combination chemotherapy in vitro with cis-dichlorodiammineplatinum (II) Cancer Treat Rep 60(11): 1619-1625). The value at an Ara-C concentration of $10^{-6}$M, which is within an effective blood concentration range of the drug, was extremely high (0.188). Thus, it became clear that, quite dissimilar to FNIII14, D-Glu-FNIII14 exerts a highly synergistic effect, and provides an efficient therapeutic effect in practical cases.

Combination Index $(CI) = V_3/(V_1 \times V_2)$ $V_1$=cell viability when exposed to the anticancer agent at a certain concentration
$V_2$=cell viability when exposed to the test substance at a certain concentration
$V_3$=cell viability when exposed to a combination of the anticancer agent and the test substance
CI=1: additive effect
CI>1: antagonistic effect
CI<1: synergistic effect Example 5

The effect exerted by D-Glu-FNIII14 obtained in Example 1 in mice was checked in the following manner.

Six-week old SCID mice (Charles River Laboratories, Japan) were divided into groups of six mice, and each group was irradiated with a radiation of 4 gray. Thereafter, $5 \times 10^6$ U937 cells were intravenously administered into the tail vein of each mouse. On day 7 after the administration, 1.0 mg or 0.5 mg of FNIII14 or 1.0 mg or 0.5 mg of D-Glu-FNIII14 was injected into the tail vein of each mouse, and, simultaneously, AraC (20 mg) or physiological saline was intraperitoneally administered. Thereafter, the mice were reared under normal rearing conditions, and the effect of each peptide was evaluated. The results are shown in FIG. 4.

Figure 4:
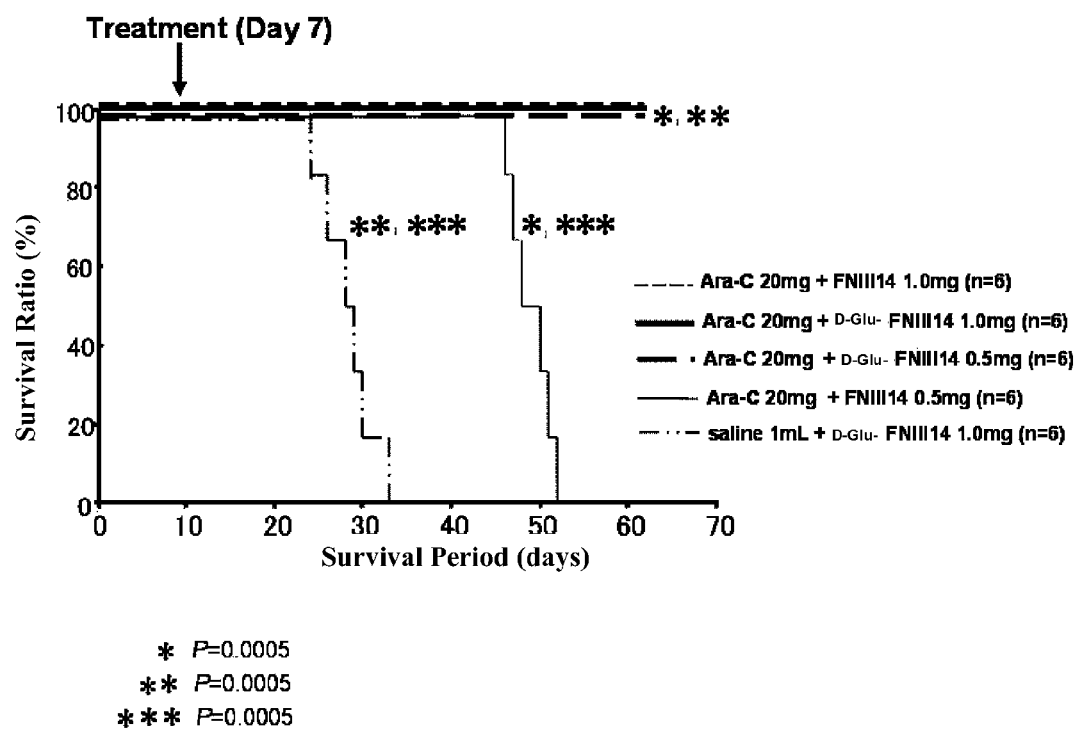
FIG. 4 is a graph showing an effect of the polypeptide according to Example 1 of the invention on the enhancement of activity of an anticancer agent in mice.

As shown in FIG. 4, mice in the groups to which D-Glu-FNIII14 was administered survived 60 days or longer regardless of whether the dose was 1 mg or 0.5 mg, indicating that complete remission can be expected. In the groups to which FNIII14 was administered, mice survived 60 days or longer when the dose was 1 mg, similarly to the group to which D-Glu-FNIII14 was administered; however, the survival ratio of the mice became 0 on or around day 50 when the dose was 0.5 mg. These results indicate that a minimum required dose of D-Glu-FNIII14 is half of that of FNIII14 not containing the D-form glutamic acid, and that the effect of D-Glu-FNIII14 on the enhancement of the activity of the anticancer agent is surprisingly at least two times higher than that of FNIII14. Considering the results shown in FIG. 2 and FIG. 3, the effect is expected to be obtained even with lower doses.

As described above, it was demonstrated that the D-form amino acid residue-containing FNIII14 has a strong effect in terms of enhancement of the activity of an anticancer agent that is used with the D-form amino acid residue-containing FNIII14, and synergistically increases the effect of the anti-cancer agent when used in combination with the anticancer agent.

Therefore, according to the invention, an activity enhancer for an anticancer agent capable of enhancing the therapeutic effect of an anticancer agent that is used together with the activity enhancer, and a pharmaceutical composition for treatment of a cancer that includes the activity enhancer, can be provided.

The disclosure of Japanese Patent Application No. 2011-054475, filed Mar. 11, 2011, is incorporated herein by reference in its entirety.

All publications, patent applications, and technical standards mentioned in this specification are herein incorporated by reference to the same extent as if each individual publication, patent application, or technical standard was specifically and individually indicated to be incorporated by reference.

The invention claimed is:

1. An activity enhancer for an anticancer agent against leukemia, comprising, as an active ingredient, a D-form amino acid residue-containing FNIII14 polypeptide, the D-form amino acid residue-containing FNIII14 being a polypeptide FNIII14 set forth in SEQ ID NO: 1 in which a glutamic acid residue that is an amino acid residue at position 2 is a D-form amino acid residue.

2. The activity enhancer for an anticancer agent against leukemia according to claim 1, wherein the D-form amino acid residue-containing FNIII14 polypeptide is a D-form amino acid residue-containing FNIII14 polypeptide multimer.

3. The activity enhancer for an anticancer agent against leukemia according to claim 1, wherein the anticancer agent is at least one selected from the group consisting of cytarabine (AraC), enocitabine, and elacytarabine.

4. A pharmaceutical composition for treatment of a leukemia, comprising the activity enhancer for an anticancer agent against leukemia according to claim 1 and a pharmaceutically acceptable carrier.

5. The pharmaceutical composition according to claim 4, further comprising an anticancer agent.

6. An anticancer therapeutic agent set comprising a first container section in which the activity enhancer for an anticancer agent against leukemia according to claim 1 is contained, and a second container section in which an anticancer agent is contained.

7. A polypeptide that is either one of the following peptides:
(a) a polypeptide which is set forth in SEQ ID NO: 1, and in which a glutamic acid residue that is an amino acid residue at position 2 is a D-form amino acid residue; or
(b) a polypeptide which is a multimer, of which a constituent unit is the polypeptide (a).

8. The activity enhancer for an anticancer agent against leukemia according to claim 1, the D-form amino acid residue-containing FNIII14 being a polypeptide FNIII14 set forth in SEQ ID NO: 1 in which a glutamic acid residue that is an amino acid residue at position 2 is a D-form amino acid residue.

9. A method for treating a leukemia, the method comprising administering, to a patient in need of treatment of leukemia, the activity enhancer for an anticancer agent against leukemia according to claim 1.

* * * * *